United States Patent [19]

Barr et al.

[11] Patent Number: 5,593,697
[45] Date of Patent: Jan. 14, 1997

[54] SINGLE DOSE VACCINATION SYSTEM

[75] Inventors: Ian G. Barr; William J. Thiel, both of Parkville, Australia

[73] Assignee: CSL Limited, Parkville, Australia

[21] Appl. No.: 119,174

[22] PCT Filed: Mar. 25, 1992

[86] PCT No.: PCT/AU92/00124

§ 371 Date: Nov. 17, 1993

§ 102(e) Date: Nov. 17, 1993

[87] PCT Pub. No.: WO92/17165

PCT Pub. Date: Oct. 15, 1992

[30] Foreign Application Priority Data

Mar. 26, 1991 [AU] Australia .................................. PK5268

[51] Int. Cl.⁶ .................................. A61F 2/02; A61K 9/16; A61K 9/50
[52] U.S. Cl. .................................. 424/490; 424/424; 424/426; 424/501; 514/772.3
[58] Field of Search .................................. 424/423, 424, 424/425, 426, 487, 488, 490, 501; 514/772.3

[56] References Cited

U.S. PATENT DOCUMENTS

| | | | |
|---|---|---|---|
| 5,011,692 | 4/1991 | Fujioka et al. | 424/426 |
| 5,026,559 | 6/1991 | Eichel et al. | 424/490 |

FOREIGN PATENT DOCUMENTS

| | | |
|---|---|---|
| 79120/91 | 2/1992 | Australia . |
| 0212745 | 3/1987 | European Pat. Off. . |
| 0408496 | 1/1991 | European Pat. Off. . |
| 1594514 | 6/1970 | France . |
| 3-197421 | 8/1991 | Japan . |
| 2048671 | 12/1980 | United Kingdom . |
| 2170210 | 7/1986 | United Kingdom . |
| 87/06828 | 11/1987 | WIPO . |
| 90/11070 | 10/1990 | WIPO . |

OTHER PUBLICATIONS

Controlled Drug Delivery, Fundamentals and Applications, Second Edition Robinson and Lee, Eds., Marcel Dekker, Inc. pp. 481–516.
Drug Delivery Devices, Fundamentals and Applications, Tyle, Ed., Marcel Dekker, Inc. pp. 33 and 591–600.
Biodegradable Polymers As Drug Delivery Systems, Ed. M. Chasin and R. Langer (Marcel Dekker), Chapter 1, pp. 5–8.
Agyilirah, G. A. and Banker, G. S., in Polymers For Controlled Drug Delivery, Tarcha, Ed., Chapter 3, "Polymers for Enteric Coating Applications", CRC pp. 40–41, CRC Press (1991).
Supplementary Search Report for EPO Application No. 92907229.6 (mailed Apr. 13, 1994).
International Search Report for International Application No. PCT/AU92/00174 (mailed 1 Jul. 1992).
Chemical Technology Reivew, No. 177; "Sustained Release Medications"; edited by J. C. Johnson (New Jersey); issued 1980; see pp. 179–180.

*Primary Examiner*—Carlos Azpuru
*Attorney, Agent, or Firm*—Fish & Richardson, P.C.

[57] ABSTRACT

The invention provides a pharmaceutical or veterinary implant, which when parenterally administered releases a pulse of at least one biologically active material at a controllable time interval after implantation. The implant comprises the biologically active material; an excipient comprising at least one water soluble material and at least one water insoluble material; and a polymer film coating adapted to rupture at a predetermined period of time after implantation, and wherein the excipients and polymers are biocompatible. The biologically active material is selected from the group consisting of antigens, antibodies, hormones, growth promotants, antibiotics, nutrients, minerals and vitamins. Preferably the excipient comprises a combination of two or more water-soluble and water-insoluble materials.

15 Claims, 5 Drawing Sheets

SINGLE DOSE VACCINATION SYSTEM

This invention relates to biocompatible or biodegradable implants, for veterinary or human applications, and especially to such implants which can be administered subcutaneously or intramuscularly.

The invention is particularly, but not exclusively, concerned with biocompatible or biodegradable implants for the administration of antigens to animals including man, which provide a pulsed release of antigen at a period of time after implantation, ie. in which release is delayed. The time delay can be controlled by varying the formulation of the implant. Although the invention is described by reference to vaccines comprising an antigen, optionally administered together with an adjuvant, the person skilled in the art will readily appreciate that the invention is equally applicable to the pulse release of any agent. Examples of such other agents include antibodies, hormones, growth promotants, antibiotics, nutrients, minerals, vitamins, and so on.

For the purposes of the present specification "biocompatible" is to be taken to mean that all components of the implant should be physiologically tolerable and should not cause an adverse local or systemic response when implanted. "Biodegradable" means that the components are degraded into harmless components which are either metabolized or excreted.

BACKGROUND AND PRIOR ART

It has long been appreciated that multiple injections of certain antigens are required to elicit an adequate immune response and production of antibodies [1]. A suitable and widely used method is the sub-dermal or subcutaneous injection of antigen together with one or more adjuvants in liquid formulations by needle. However, the necessity for such multiple injections has greatly increased the cost and inconvenience of immunization programes both in human and veterinary medicine. Furthermore, in third world countries, not only has the need for such multiple injections meant that many human patients receive an incomplete course of immunisation, but conditions are often such that liquid formulations for injections are subject to adverse storage conditions, or made up under non-sterile conditions.

In veterinary and human medicine there is therefore a need for dosage forms which after a single administration result in the release of antigen at different times [5,7]. The release may be continuous or occur as one or more pulses delayed for a period of time after administration. Such a delayed release implant has considerable potential in veterinary medicine as it allows two or more doses of antigen to be administered in a single handling of the animal, resulting in significant cost saving. The use of such a delivery system in human medicine in third world countries would also contribute significantly to savings in utilization of scarce medical resources, as co-administration of immediate and delayed release implants permits a second pulse of antigen to be released a set time period after implantation. This ensures that the booster dose of antigen is received, which in many vaccines is essential to achieve appropriate efficacy.

Small, usually cylindrically shaped implants, which are inserted into the subcutaneous tissue using a specially designed implanter, have been widely used as controlled release delivery systems in veterinary medicine (2,3). The polymers and excipients used in such devices must be biocompatible (2) and or biodegradable (2,16,17). Applications suggested for veterinary controlled release devices include disease prevention, growth promotion, vaccination, fertility control, and supplementation of nutritional agents (4,5). Recently, Caster, Luttinger and Gardner [4] have reviewed the use of controlled release parenteral systems for veterinary use and tabulate commercially available products and delivery systems under development. In humans, subcutaneous delivery systems based on Silicone tube implants have been used to deliver steroids and anti-inflammatory drugs (6). Modulated and triggered drug delivery systems which use pH sensitive polymers in subdermal devices are being developed (19).

In the application of an implant for antigen delivery (vaccination) it may be preferable to release antigen as a pulse rather than continuously over a period of time. Pulsed release mimics most closely the administration of liquid injections at set time intervals [1], which is the current regimen used to obtain protection from disease. Some pulsed systems for oral delivery have been described in which the dose is divided, the second portion being released some hours after administration [10], or alternatively comprising a number of pellets which can rupture at controlled times over a twelve hour period [11].

Australian Patent No. 601443 (WO-87/06828) describes an implant which releases a peptide or protein in a substantially continuous manner at a substantially constant rate over a desired period, without any significant delay phase. The implant comprises a permeable, non-dissolving polymeric coating which forms a release rate limiting barrier, and which does not degrade over the life of the implant International Patent Application No. WO 91/04052 describes a solid vaccine composition containing an antigenic substance, saponin, and a polycationic adjuvant, which may be formulated as an implant in which pulsed release may be achieved by coating the vaccine with different thicknesses of polymer.

International Patent Application No. WO 87/06129 describes an implant formulation in which controlled release of active agent is achieved by using a plurality of biodegradable microcapsules within a biodegradable polymeric implant. An optional coating may be provided for impact resistance; this coating is biodegradable at a more rapid rate than the biodegradable micro capsules.

International Patent Application No. WO 91/0713 describes an oral contraceptive dosage form providing a pulsed dose of oestrogen and progesterone via immediate release of an outer, biodegradable coat on an implant, followed by delayed release of oestrogen via an osmotic device consisting of two compartments, of which the second compartment contains salt and has osmotic swelling properties, which force the active agent out through a pore in the outer coat. None of these three specifications discloses the combination of water soluble and water insoluble excipients, and in particular a water insoluble, swellable excipient is not disclosed.

A microencapsulated liposome system for vaccine delivery is described by Cohen, Chow and Langer [12]. Delayed pulsed release of FITC-BSA is achieved using the delivery system. However, there is a continuous release at low levels between the two pulses; the delayed pulse occurs some 17–95 days after the initial release of FITC-BSA. U.S. Pat. No. 4,900,556 describes biologically active agents entrapped in liposomes which are protected from the biological environment by microencapsulation.

We have now designed delayed pulsed release implants which satisfy the above requirements, at least in part, and which can be prepared using readily available pharmaceutical excipients and techniques already used in the known prior art of tabletting and film coating. This specification describes implants which are designed to give a delayed pulsed release. When implanted in conjunction with an immediate release implant (or alternatively a conventional liquid injection) the combination is capable of releasing an initial pulse of antigen, then a second antigen pulse typically 10–60 days after implantation (delayed release). For many applications the preferred time is 20–60 days.

SUMMARY OF THE INVENTION

The present invention seeks to provide a biocompatible implant which will provide a delayed pulsed release of antigen at a predetermined time period after implantation. During the delay period prior to pulsed release, there is no significant release of antigen from the device. The implantation of one or more implants giving (i) immediate, and (ii) delayed pulsed release of antigen closely mimics the multiple vaccination regime used with conventional liquid formulations given a set time interval apart. When the delayed release implant is administered, vaccination can be completed in a single administration, a major advantage if the vaccine requires two doses for full efficacy. It will be clearly understood that for the purposes of this invention, antigen may be given with or without adjuvant, and that normal pharmaceutically or veterinarily acceptable carriers or excipients may be used. It will be further understood that the invention is applicable to the administration of more than one biologically active material within a single implant.

According to one aspect of the present invention, there is provided a pharmaceutical or veterinary implant, which when parenterally administered releases a pulse of at least one biologically active material at a controllable time interval after implantation, said implant comprising:

a) the biologically active material;

b) an excipient comprising at least one water soluble material and at least one water insoluble material; and c) a polymer film coating adapted to rupture at a predetermined period of time after implantation, wherein the excipients and polymers are biocompatible.

The biologically active material is suitably, but not necessarily selected from the group consisting of antigens, antibodies, hormones, growth promotants, antibiotics, nutrients, minerals and vitamins. Where the biologically active material is an antigen, it may optionally be accompanied by an adjuvant.

Preferably the excipients comprise a combination of two or more water-soluble and water-insoluble materials, of which the latter may advantageously be swellable.

A preferred water-soluble excipient is a sugar-based material such as lactose, but those skilled in the tabletting art will appreciate that other biocompatible, and preferably biodegradable materials can also be used.

The function of the water insoluble materials is twofold:

a) to provide a physical form to the implant which does not break up when it hydrates, and b) to provide an excipient (disintegrant) which swells when hydrated. The preferred water insoluble excipient to provide the physical form is calcium phosphate (Emcompress® [13]) and a preferred swellable excipient is sodium starch glycolate (Explotab® [13]). Other preferred water insoluble excipients are stearic and palmitic acids. Those skilled in the tabletting art will appreciate that other insoluble compressible excipients and swelling excipients (disintegrants) may be used, and that selection of suitable combinations is a matter of routine optimization.

The biologically active material and excipients are compressed into shaped cores or tablets using known techniques; preferably the cores are cylindrical in shape, so as to produce implants which are adapted for implantation using a commercially-available device, for example, that described in reference 3. The shaped core is then coated with a polymer to form a film coating, for example, by spraying [8,9]. One or more layers of different polymer films may be used. Preferably, the polymer coating when exposed to normal physiological pH of 7.3–7.4, will rupture after a period of time (typically 14 to 45 days), thus releasing the biologically active material as a delayed pulse.

In a preferred embodiment of the invention, two different polymer films are applied to the compressed cores using standard film coating procedures. The polymer films used are:

i) a bilayer coating comprising an insoluble biocompatible film and an enteric (pH sensitive) polymer, and, ii) a single film comprising a mixture of insoluble and biodegradable polymer.

The implants of the invention may be prepared by any suitable techniques known per se from the prior tabletting art.

For example, a mixture of the water soluble and insoluble excipients with the appropriate amount of the active ingredient may be compressed into tablet-shaped solid cores of the required size and shape, which are then coated using conventional techniques, e.g. by spraying with a solution or dispersion of the coating material in a pan coater or a fluidized bed coater.

According to a second aspect of the invention, there is provided a method of administration of a biologically active material to a mammal, comprising the step of implantation of an implant as described herein.

BRIEF DESCRIPTION OF THE DRAWINGS

FIG. 6 shows an implant designed so as to give two delayed pulsed doses separated by a time interval, while FIG. 6A shows a profile of the time course of antigen release from such an implant.

DETAILED DESCRIPTION OF THE INVENTION

In the discussion hereinbelow, it will be clearly understood that reference to antigen or antigen plus adjuvant is equally applicable to other biologically active materials which may generally be referred to as the payload.

BIOCOMPATIBLE BILAYER FILM

Figure 1:
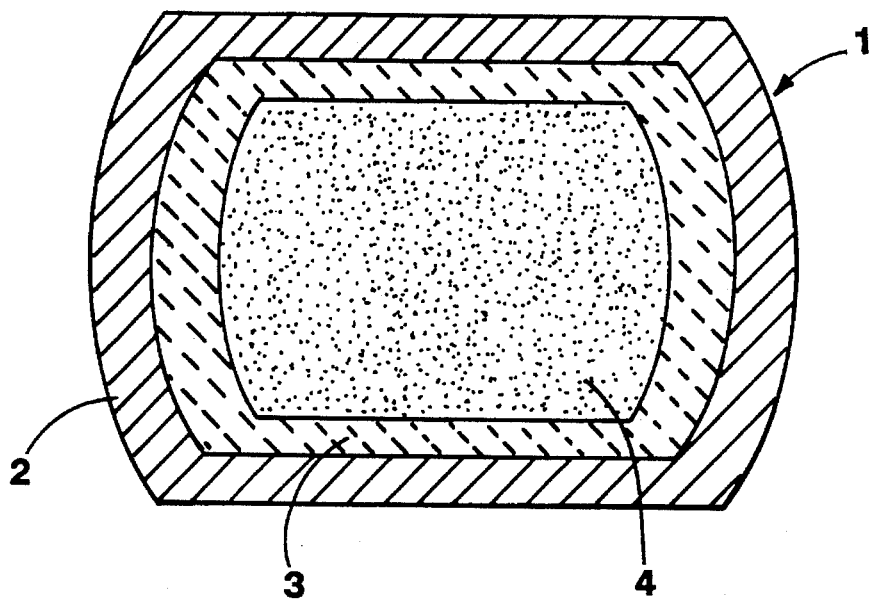
FIG. 1 represents a longitudinal section of a coated implant according to a preferred embodiment of the invention.
Figure 2:
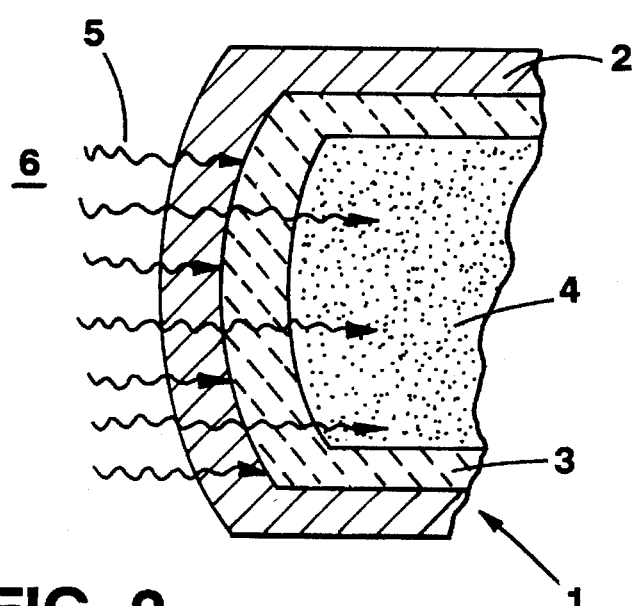
FIG. 2 schematically illustrates the method of control of access of physiological fluid to the core of the implant according to the invention.

The bilayer film coating forms an impermeable barrier to the antigen until such time as the inner, pH sensitive film fails due to ingress of physiological fluid (pH 7.3–7.4), causing partial dissolution of the inner film. This is illustrated in FIG. 1, which shows an implant 1 in which the insoluble outer film 2 controls the degree of access of the physiological fluid to the inner film 3, which is soluble at physiological pH. By varying the thickness of the outer film 2, access of the physiological fluid to the inner film 3, and hence the time before failure of the inner film occurs, can be controlled. Failure of the inner film 3 permits the swellable excipient (disintegrant) to exert a force on the outer film 2, which then ruptures, releasing the core content 4 as a pulse. The antigen released by this rupturing implant may be soluble or insoluble. Release in the context of a delayed release vaccine delivery system means that the antigen/adjuvant contacts tissue in the host animal. These general features are illustrated in FIG. 2, in which 5 indicates physiological fluid moving from the subcutaneous tissue 6 the outer and inner films 2 and 3 respectively to reach the core 4.

Preferred inner and outer films (FIG. 1) comprise the pH sensitive Eudragit® S100 [13] and an insoluble film formed from Eudragit NE30D aqueous acrylic dispersion [13]. These commercially available polymers have been widely used in oral sustained/controlled release products intended for gastrointestinal use. The Eudragit® S100 film dissolves at pH>7.0 [14], ie is soluble at tissue pH after implantation. This film is impermeable to high molecular weight peptides or proteins, and hence is impermeable to antigens. Thus no significant release occurs until the Eudragit® S film splits due to:

i) partial dissolution by the physiological fluid or when present, and ii) the swelling action of the disintegrant (Explotab®) in the core.

Deletion of Explotab® from the core results in an implant which does not rupture as rapidly, but which is still capable of delivering antigen and eliciting an immune response. The film formed from Eudragit NE30D is insoluble over the range pH 1–8 [14] and forms an insoluble outer coat over the film designated S, which is soluble at pH>7.0. This outer film controls the access of physiological fluid to the inner Eudragit S film (FIG. 2) and hence the rate of chemical degradation of the S film. The thickness and permeability of the Eudragit® non-soluble (N) film can be varied by addition of another polymer to control the time interval before delayed pulsed release of the payload (antigen) in the core. A preferred polymer to modify the permeability of the Eudragit N film is hydroxypropyl methylcellulose (HPMC) [13]. The N film is preferably heat treated to complete the latex coalescence to form a continuous film [18].

Those skilled in the art of polymeric film coating will appreciate that other combinations of pH sensitive and insoluble polymeric materials can be used to achieve a similar delayed pulsed release. Examples of such polymers include (but are not limited to):

insoluble polymers, ethylcellulose, silicone, polypropylene, polyethylene, nylon and polyesters;

pH sensitive (enteric) polymers, cellulose acetate phthalate, hydroxypropyl methylcellulose acetate succinate, hydroxypropyl methylcellulose phthalate, cellulose acetate trimellitate and Eudragit® L (acrylic resin).

Apart from the ingredients already listed, the implants of the invention may be formulated with conventional additives known per se in the tabletting art, especially lubricating agents, such as magnesium stearate. Additives which enhance the immune response may also be added. These are loosely termed adjuvants, examples of which include but are not limited to aluminium salts, calcium phosphate, saponin, Quil A, dextran sulphate, DEAE dextran, muramyl dipeptide, DDA (dimethyl dioctadecyl ammonium bromide), Montanide 451, LPS (lipopolysaccharide) and various bacterial wall extracts.

PARTIALLY BIODEGRADABLE SINGLE FILM

Using the same materials to formulate the implant core, a film coating comprising a mixture of ethylcellulose (EC) and copolymer of glycolic and lactic acid (PLGA) was applied. The dosage form is similar to that illustrated in FIG. 1, except that the bilayer Eudragit® N&S films are replaced by a single film comprising a mixture of EC/PLGA polymers. Ethyl cellulose [13] is an insoluble polymer, thus when the PLGA polymer in the EC/PLGA film hydrolyses the film become porous, allowing release of the payload. The rate of hydrolysis of PLGA depends on the ratio of lactic to glycolic acid in the copolymer [17], and is typically 30–180 days. A preferred polymer is "Lactel" Birmingham Polymers grade 50/50 or 65/35 DLPLG.

Microencapsulation with pure PLGA copolymers [17] yields a totally biodegradable system. However, pure PLGA has a low glass transition temperature (Tg) [17], and is difficult to film coat onto implant cores using conventional film coating equipment, as the film becomes tacky causing the cores to aggregate and then separate which leads to picking (holes forming in the film). A blend of EC/PLGA has a higher Tg, thus a EC/PLGA mixture in methylene chloride solvent forms a polymer solution which can be readily sprayed in conventional film coating equipment to form a high quality partially bioerodable film.

The PLGA content of the mixture film can be as low as 1–5% or up to 90% on a dry weight basis. The films are totally impermeable to water soluble compounds with a molecular weight >1000 Daltons until the PLGA partially hydrolyses, forming pores in the EC which then permits release. The time interval before this occurs depends on the grade of PLGA used [16], the wt % in the film and the percentage of ethyl cellulose. Those skilled in the art will also appreciate that other biodegradable polymers may be used, including polyhydroxybutyrate, polycaprolactone, polyortho esters, polyacetals, cyanoacrylates and poly (glutamic acid) copolymers.

Once formed, the implants of the invention have the advantage that they may be stored without refrigeration for considerable periods. The implants may be placed in the body of an animal or human subject by any suitable technique, for example, intramuscular or subcutaneous injection, or by subdermal surgical implantation using conventional clinical or veterinary techniques.

One specific application of particular interest is the administration to sheep of a vaccine against caseous lymphadenitis, a chronic disease of sheep caused by *Corynebacterium pseudotuberculosis* and characterised by the formation of abscesses in the lymph nodes [15]. Other vaccines against bacterial, viral, fungal or protozoal infections of animals or humans may also utilize the implants of the invention. Hormones or vitamins may also be administered using the implants of the invention. Vaccines include, but are not limited to, clostridial vaccines, such as *Clostridium botulinum* toxoid, babesiosis, leptospirosis, erysipelas, foot rot, canine parvovirus, and *Escherichia coli*. Hormones include, but are not limited to, luteinizing hormone releasing hormone (LHRH).

However, the invention is not limited to this particular application and may be used for any suitable peptide or protein antigen combinations.

By way of example, caseous lymphadenitis (CLA) toxoid, tetanus toxoid, *Clostridium botulinum* toxoid, vitamin B12 and human haemoglobin have been successfully incorporated into, and shown to be released from, implants in accordance with the invention. Human haemoglobin and vitamin B12 have been used as model "antigens" for in vitro release studies because of their ease of detection.

The invention will be further described and illustrated by way of reference only to the following non-limiting examples, in which all parts and proportions are by weight.

EXAMPLE 1

General Method for Preparation of Implants

The water-insoluble excipient (e.g., calcium phosphate) was thoroughly mixed with the active ingredients in an amount sufficient to give the required dosage in the final product.

The water-soluble excipient (e.g, lactose) was then added, together with other additives, e.g. a lubricating agent such as magnesium stearate, and mixed in to form a dry powder. The powder was then compressed into cylindrical-shaped "cores" of the desired size and shape.

The compressed cores were coated in a pan coater by spraying with a solution or dispersion of the different coating materials in an amount sufficient to give implants having the required coating thickness. Where two films were desired, they were applied sequentially. Typically the implants will weigh 30–40 mg and be about 2.5 mm in diameter ×3.5–4.5 mm length.

With some active ingredients such as low bulk density lyophilized powders, it may be advantageous to granulate using wet or dry methods before compression of the mixture into implants.

EXAMPLE 2

Delayed Pulsed Release Implants Containing 2 mg Human Haemoglobin

Using the general method of Example 1, implant cores were prepared based on the following formulation:

| Material | Core Formulation | | |
|---|---|---|---|
| | Nominal Amount | Mass/core | wt % |
| Calcium Phosphate (Emcompress ®) | 90 ratio[a] | 25.82 mg | 78.2 |
| Lactose | 10 | 2.87 mg | 8.7 |
| Human Haemoglobin | | 2.00 mg | 6.1 |
| Explotab | 6% | 1.98 mg | 6.0 |
| Magnesium Stearate | | 0.33 mg | 1.0 |
| TOTAL | | 33.00 mg | 100.0 |

| Material | Coating Formulation | | |
|---|---|---|---|
| | Nominal Amount | Mass/core | wt % HPMC in film |
| Eudragit S100[b] (inner film) | 20% | 4.6 mg | not applicable |
| Eudragit NE30D[c] (outer film) | 10% | 3.3 mg | 3% |
| | 10% | 4.2 mg | 5% |
| | 10% | 4.2 mg | 7% |

[a] ratio of insoluble calcium phosphate to soluble lactose.
[b] plasticised with 24% dry wt dibutyl phthalate, polymer sprayed as a 7% wt solution in isopropyl alcohol and ethanol (50:50).
[c] Eudragit NE30D aqueous dispersion containing 3,5 or 7% wt water soluble hydroxypropyl methylcellulose (HPMC)

In vitro testing of the release characteristics of the implants was performed by placing single units in tubes containing 3 mL of buffer. Ten implants of each coating composition (3, 5 and 7% HPMC in the N film) were placed in isotonic phosphate buffered saline, pH 7.3 (subcutaneous physiological pH) and pH 5.8 and stored at room temperature (20°–25° C.). As the films hydrate the HPMC dissolves and leaches out of the N film, producing a porous structure. At both pH 5.8 and 7.3, solvent (water) will move through the N & S films and hydrate the implant core. This will cause the Explotab to swell, causing a stress in the N/S film combination. The S film will dissolve at pH 7.3, the rate of dissolution depending on the permeability of the N film (FIG. 2). Once significant S film erosion occurs, the internal pressure in the core ruptures the films, releasing the core contents. Testing at pH 5.8 will result in no dissolution of the S film; the bilayer N/S combination will remain intact. Thus, rupture of the implant at pH 5.8 is caused solely by the resulting force generated by swelling of the Explotab® (disintegrant). On visual observation of the implants over 35 days, the release of human haemoglobin was detected visually by its red-brown colour when the implants ruptured, ie. the film split to an extent that the core contents were clearly visible.

Figure 3:
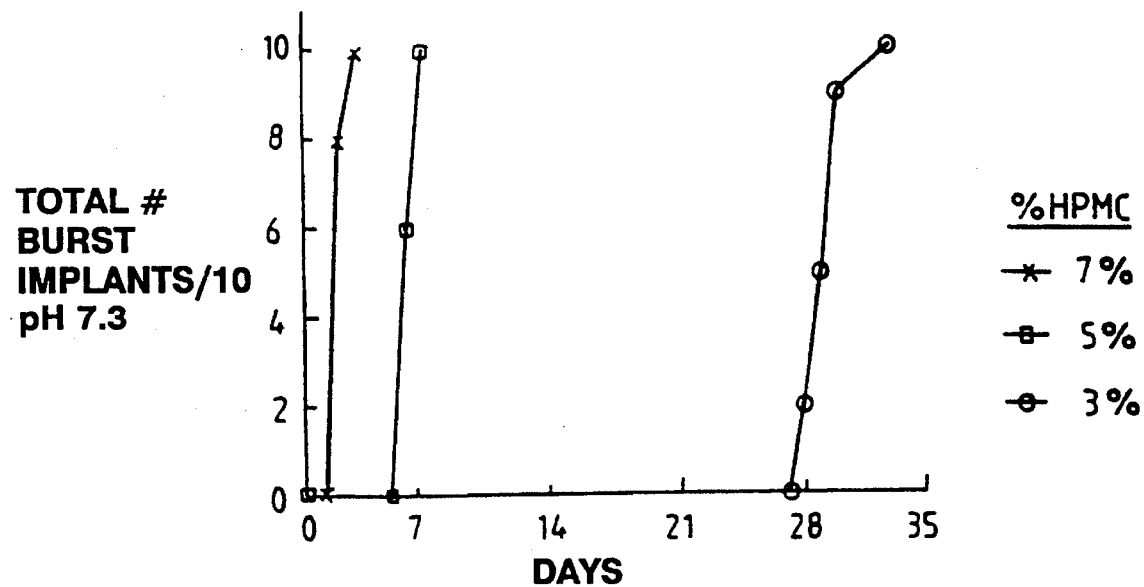
FIGS. 3 and 3A, respectively, show results of comparative studies of rupture of implants according to the invention at pH 7.3 and pH 5.8 as a function of the percentage of hydroxypropylmethyl cellulose in the coating film.
Figure 3A:
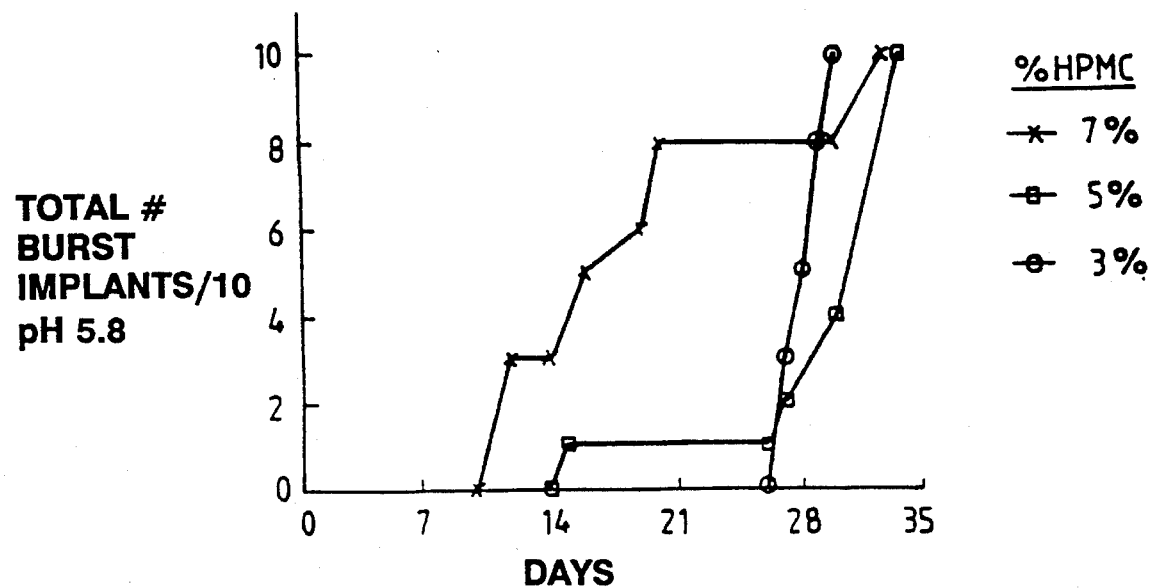

The results are shown in FIGS. 3, 3A, 4 and 4A as the cumulative number of implants releasing haemoglobin or ruptured at both pH 7.3 and 5.8. FIGS. 3 and 3A, respectively, show the times at which implants ruptured as a function of the % HPMC in the N film, when placed in pH5.8 or 7.3 medium. At 7% HPMC in the N film (ie the most permeable outer film), little protection of the S film was provided at pH 7.3; rupture occurred in all ten implants by day 3. In contrast, at pH 5.8, rupture did not commence until day 9 and took until day 30 before all implants burst.

FIG. 3 and 3A, respectively, show that for implants with N films containing 5% HPMC, rupture occurred between day 5–7 at pH 7.3 and between day 13–34 at pH 5.8. Using 3% HPMC in the N film (ie least permeable film), rupture of the implants was delayed until day 26–33 at both pH 5.8 and 7.3. The lack of correlation of rupture time with pH shows that at this HPMC level swelling of Explotab® within the implant core was the major cause of film rupture.

Figure 4:
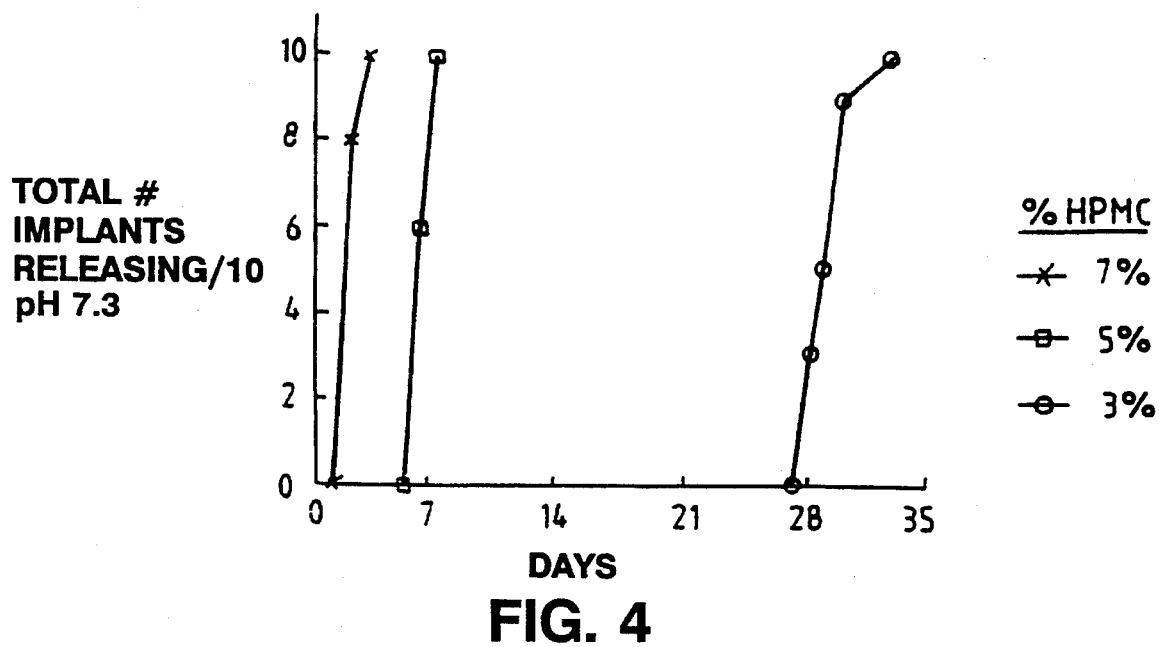
FIGS. 4 and 4A, respectivey, shows release of haemoglobin with time from implants according to the invention at pH 7.3 and pH 5.8.
Figure 4A:
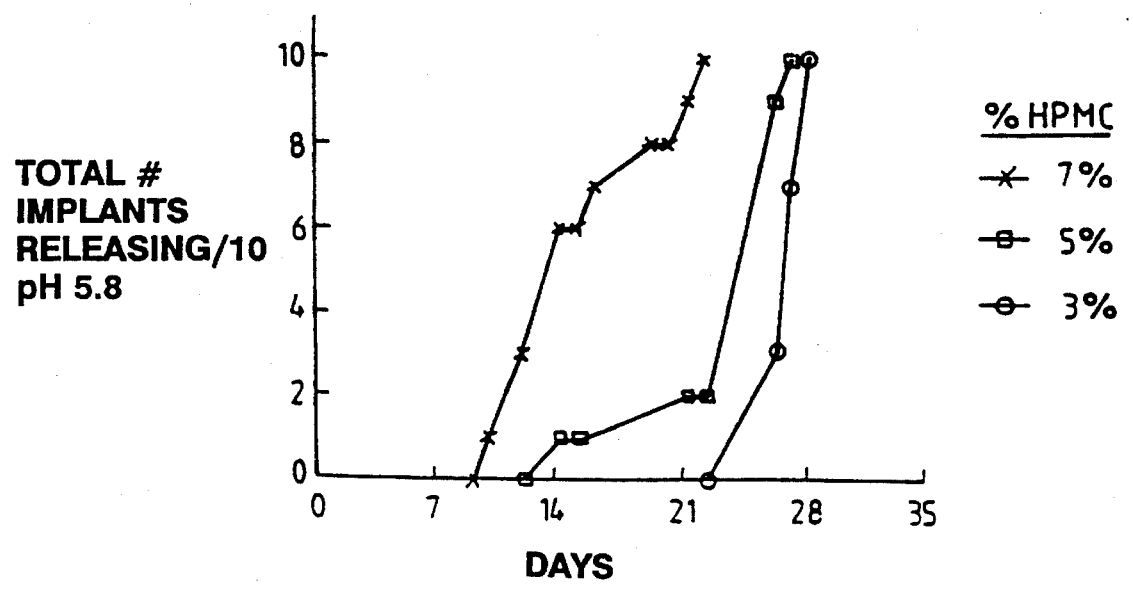

FIG. 4 and 4A, respectively, are plots showing the time at which the implants were recorded to be releasing haemoglobin, as a function of the % HPMC in the N film, when placed in medium at pH 5.8 and 7.3. A strong correlation between the release time (FIGS. 4 and 4A) and implant rupture (FIGS. 3 and 3A) was observed.

FIGS. 3, 3A, 4 and 4A show that minimal release of the water soluble haemoglobin occurred before film rupture. Thus a vaccine delivery device based on the formulation using 3% HPMC in the N film could be expected to give no antigen release before day 26.

Implants coated with S film alone release and rupture in pH 7.3 buffer in less than twenty four hours, without the protection afforded by the outer N film. In FIGS. 3A and 4A, the results at pH 5.8 show that as the level of HPMC in the N film decreases, rupture of the implants takes longer to occur. Thus varying the N film permeability also affects the rate at which buffer enters the core to activate the swellable Explotab®.

A number of formulation variables have been explored and found to interact to control the time before film rupture and payload release occurs. The variables are;

(i) HPMC level in the N film

EXAMPLE 3

Formulation Studies with Delayed Pulsed Release Implants Containing 2 mg Human Haemoglobin Using the method of Example 1, and the formulation described as Example 2, implants were manufactured in which the formulation was varied by changing the Emcompress®/lactose (E/L) ratio, thickness of the N film and the amount of Explotab® in the core. The quantity of HPMC in the N film was kept constant (3% wt) and the thickness of the S film was constant at a nominal 25% wt of the core mass. The release studies described in Example 2 were performed in pH 5.8 and 7.3 buffer at 37° C. The observed haemoglobin release and implant rupture times are shown in Table 1 as the range recorded for ten implants of each formulation tested at each pH.

TABLE 1

Delayed Pulsed Release Implants containing 2 mg human haemoglobin

| Group | E | L | Explotab | S | N | HPMC | Release | Rupture | Buffer pH |
|---|---|---|---|---|---|---|---|---|---|
| 1 | 90 | 10 | 10 | 25 | 20 | 3 | 15–18 | 15–18 | 5.8 |
|   |    |    |    |    |    |   | 13–13 | 13–15 | 7.3 |
| 2 | 90 | 10 | 6  | 25 | 20 | 3 | 18–25 | 41–67 | 5.8 |
|   |    |    |    |    |    |   | 21–27 | 35–46 | 7.3 |
| 3 | 99 | 1  | 6  | 25 | 20 | 3 | 25–25 | 25–25 | 5.8 |
|   |    |    |    |    |    |   | 18–25 | 18–25 | 7.3 |
| 4 | 100| 0  | 6  | 25 | 20 | 3 | 29–31 | 29–31 | 5.8 |
|   |    |    |    |    |    |   | 18–29 | 18–29 | 7.3 |
| 5 | 99 | 1  | 6  | 25 | 50 | 3 | 32–41 | 32–41 | 5.8 |
|   |    |    |    |    |    |   | 29–35 | 29–35 | 7.3 |
| 6 | 100| 0  | 6  | 25 | 50 | 3 | 39–43 | 39–43 | 5.8 |
|   |    |    |    |    |    |   | 25–39 | 25–39 | 7.3 |
| 7 | 99 | 1  | 6  | 25 | 100| 3 | 53–67 | 53–67 | 5.8 |
|   |    |    |    |    |    |   | 43–49 | 41–49 | 7.3 |
| 8 | 100| 0  | 6  | 25 | 100| 3 | 53–63 | 53–63 | 5.8 |
|   |    |    |    |    |    |   | 49–60 | 46–60 | 7.3 |

(ii) N film thickness (iii) S film thickness (iv) ratio of insoluble Emcompress® to soluble lactose (v) amount of swellable disintegrant (Explotab®) in the core The following examples illustrate the effect of these formulation variables. The formulation modifications are denoted by:

E/L for Emcompress®/lactose ratio,

Explotab® % wt in core, nominal amount of polymer coatings e.g. 20S meaning S film comprising 20% wt nominal of the core mass, e.g. 50 N (3% HPMC) meaning a N film of 50% wt nominal of the core containing 3% wt HPMC on a dry film basis.

Using this nomenclature the formulation tabulated at the start of this example (lowest HPMC level) is 90E/10L, Explotab 6%, 20S, 10 N (3% HPMC).

These results show that: increasing the thickness of the N film increases the time delay before release/rupture occurs (compare group 3/5/7 and 4/6/8), and increasing the level of Explotab® decreases the delay (see group 1/2).

In most cases (Table 1) rupture at pH 7.3 occurred earlier than at pH 5.8 showing the S film underwent significant erosion at pH 7.3 (partial dissolution).

Using low lactose levels (1% or absent (100E)) and N films at 50 and 100% can achieve a 40–60 day delay before pulsed release occurs (group 7 and 8).

Under physiological conditions (pH 7.3) the amount of release observed before implant rupture occurred was minimal (the exception being group 2). This is believed to be a desirable attribute for a delayed pulsed vaccine delivery system.

EXAMPLE 4

Delayed Release from Implants Containing *Clostidium botulinum* C Toxoid: Serological Response in Mice.

Mice were implanted with a single pellet formulated as described below or a liquid injection containing *C. botuli-* num C toxoid at day 0. Mice were bled regularly, and their sera assayed for the presence of antibodies to *C. botulinum* C toxin using a standard ELISA assay. The results are shown in Table 2, and demonstrate that by encapsulating the vaccine in the polymer bilayer of NE 30 D and S 100 that significant delay in seroconversion, and therefore a delay in release of the vaccine, has been achieved. After a period of time the coated pellets also release their contents, and seroconversion is achieved in mice at day 38, versus day 14 with uncoated pellets or with liquid injections containing the vaccine.

| BASIC CORE FORMULATION | |
|---|---|
| Material | mass/core |
| *C. botulinum* C toxoid (freeze dried) | 1.30 mg |
| Emcompress | 23.94 mg |
| Explotab | 1.80 mg |
| Lactose | 2.66 mg |
| Magnesium stearate | 0.30 mg |
| | 30.00 mg |

COATED PELLET

This consisted of pellets with the above core formulation which were subsequently coated with a 50% S100 film (containing 25% dibutylphthalate) followed by a 10% NE 30 D film (containing 5% HPMC) as detailed in Example 1.

TABLE 2

Murine antibody response to *C. botulinum* vaccine formulations.

| Group (N = 5) | Treatment | % Mice seroconverting for Cl. Bot. C* | | | |
|---|---|---|---|---|---|
| | | day 14 | day 24 | day 38 | day 50 |
| 1 | Pellet (Not coated) | 100 (0.86) | 100 (1.2) | 100 (1.2) | NT |
| 2 | Pellet (Coated: 50 S 10 N) | 0 | 0 | 60 (0.82) | 100 (1.16) |
| 3 | Liquid dose (Bot. C. toxid only) | 100 (0.47) | 100 (0.74) | 100 (0.95) | 100 (0.96) |

*Seroconversion was defined as sera having an optical density (O.D.) of greater than 0.3 at a dilution of 1:50, assayed by ELISA. The figures in brackets are the mean O.D. for seroconverted mice in each group, and indicate the relative amounts of specific antibody present.
NT - Not tested.

EXAMPLE 5

Immediate and Delayed Pulsed Release Implants Containing Caseous Lymphadenitis (CLA) Toxoid: In Vitro and in Vivo Testing.

An immediate release implant containing CLA toxoid and aluminium adjuvant (CLA-Al) was made using the method of Example 1. This implant is designed to break up and release the toxoid within a few hours after implantation (ie. has no film coating).

| Formulation (Immediate Release Implant) | |
|---|---|
| Material | mass/core |
| Lactose | 18.3 mg |
| 2 cpu CLA-Al toxoid | 6.7 mg |
| Magnesium Stearate | 0.3 mg |
| TOTAL | 25.3 mg |

Delayed pulsed release implants were manufactured using the method of Example 1. These contained 2 cpu (0.67 mg) of a crude preparation containing CLA toxoid (no aluminium adjuvant) incorporated into;

a) Formulation I: 90E/10L, 6% Explotab, 25S, 50N (3% HPMC), and b) Formulation II: 90E/10L, 10% Explotab, 25S, 50N (3% HPMC)

implants, as described in Examples 2 and 3.

The release of CLA toxoid into buffer at pH 7.3 (37° C.) was determined by a capture ELISA and the time to rupture by visual observation. The release/rupture characteristics observed were:

| | RANGE (days) | |
|---|---|---|
| Formulation | Release CLA Toxoid | Rupture |
| I | 21–35 | 27–46 |
| II | 14–21 | 15–19 |

The murine immune response to various administration regimes of CLA toxoid is summarized in Table 2. Group 1 represents the response measured in ten mice when two doses of CLA-Al toxoid were administered by conventional liquid injection three weeks apart. The geometric mean antibody titre was determined at 3, 6 and 12 weeks after the first dose. Group 2 is the response to a single immediate release implant; the response was greater than that to a single liquid CLA-Al injection (group 3).

TABLE 3

Murine immune response to various administration regimes of CLA toxoid

| Group 12 | Administration Regime | | Geometric Mean Antibody Titre (n = 10) | | |
|---|---|---|---|---|---|
| | Day 0 | Day 21 | Week 3 | Week 6 | Week 12 |
| 1 | CLA-Al[a] | CLA-Al[a] | 373 | 3456 | 800 |
| 2 | IR[b] | — | 985 | 1213 | 519 |
| 3 | CLA-Al[a] | — | 400 | 857 | 246 |
| 4 | IR[b] | CLA-Al[a] | 1270 | 7466 | 1234 |
| 5 | IR[b] plus DPR[c] Implant Formulation I | — | 492 | 2111 | 1176 |
| 6 | IR[b] plus DPR[c] Implant Formulation II | — | 606 | 6400 | 746 |

[a]CLA-Al, conventional liquid injection of aluminium adjuvanted CLA toxoid
[b]IR, Immediate Release Implant
[c]DPR, Delayed Pulsed Release Implant The highest mean antibody titre (6 & 12 weeks) was obtained when an immediate release implant was administered and followed three weeks later by a CLA toxoid liquid injection (group 4). The antibody response to an immediate release (IR) and a delayed pulse release (DPR) implant administered concurrently is shown as groups 5 and 6. In this case, the three week antibody response is that recorded three weeks after implantation of the IR & DPR implants. Based on previous results, the IR pellet will release its contents within 24 hours and the DPR implant should rupture approximately 21 days after implantation, releasing the second toxoid dose. The response seen in group 6 is comparable to that elicited by an immediate release implant and CLA toxoid liquid injection three weeks later (group 4). The IR & DPR formulation II combination (group 6) gave a higher six week geometric mean antibody titre than group 1 (two doses of conventional CLA-Al liquid injection given three weeks apart. Thus a combination of the immediate and delayed pulsed release implant given at day zero is able to elicit as good an immune response as CLA toxoid given as two separate liquid injections.

EXAMPLE

Ethyl Cellulose (EC)/Polylactide glycolide copolymer (PLGA) mixed film coated implants-delayed release of 2 mg vitamin B12

Implant cores were prepared using the general method of Example 1; the formulation used was

| | |
|---|---|
| Vitamin B12 | 2.00 mg |
| 80 MSD Lactose | 27.70 mg |
| 1% Mg stearate | 0.30 mg |
| | 30.00 mg |

The cores were film coated with an ethylcellulose/polyactide glycolide copolymer mixture, which was applied using a Freund Hi-Coater as a 3% solution of 1:1 EC/PLGA in dichloromethane.

The polymers used were Ethylcellulose, type N-50, Hercules, Wilmington, U.S.A. and PLGA, grade 65/35 DL-PLGA "Lactel" Birmingham Polymers, Birmingtham U.S.A.

| | |
|---|---|
| PLGA | 15 g |
| Ethyl Cellulose | 15 g |
| Dichloromethane | 970 g |
| | per 1,000 g solution |

Two different thicknesses of EC/PLGA film were applied to the implant cores. Release studies in isotonic phosphate buffer (pH 7.3) were conducted as described in Example 2.

The time to onset of vitamin B12 release is shown in Table 3. There was no release from the 4.9 mg/core implants until day 16, and 7.5 mg/core films delayed the onset of release until day 22.

TABLE 3

Release of vitamin B12 from EC/PLGA coated delayed pulsed release implants

| EC/PLGA Coating thickness (mg) | Range (days) over which release commenced | Number of implants releasing |
|---|---|---|
| 4.9 | 16–18 | 14/14 |
| 7.5 | 22–25 | 20/20 |

Figure 5:
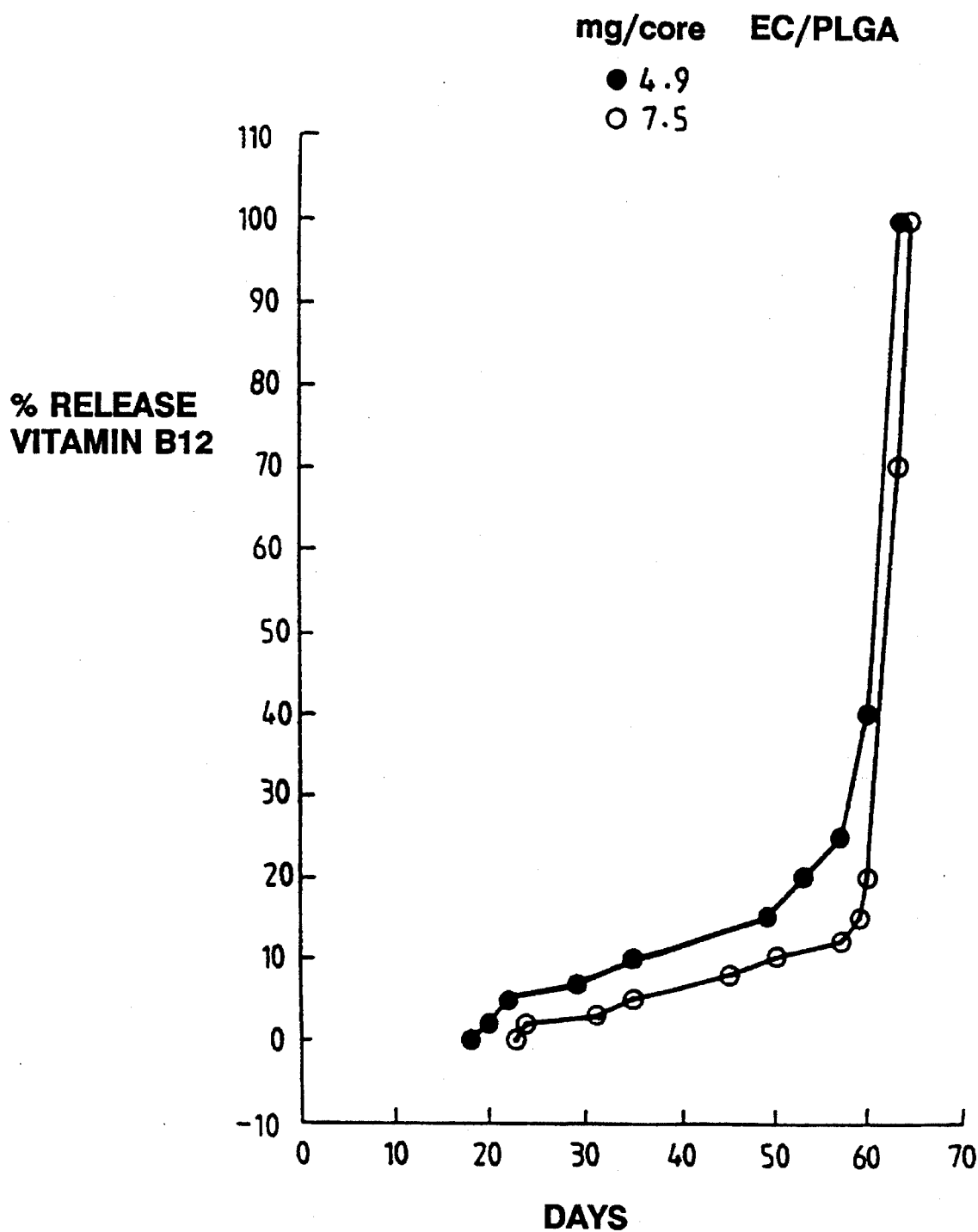
FIG. 5 shows release of vitamin B12 with time from implants according to the invention at pH 7.3.

The mean cumulative % release of the same vitamin B12 implants is shown in FIG. 5. After onset of release, 10 to 20% of the payload was released over the next 30 days, and the remaining 80% of payload was released as a pulse at day 55–60 as the PLGA polymer hydrolysed and bulk degradation occurred.

EXAMPLE 6

Extensions of the Pulsed Controlled Release Concept

The following examples are logical extensions which may be made to the delayed pulsed release concept:

(i) application of the immediate release antigen/adjuvant dose mixed with a water soluble polymer as a film on the outside of the delayed pulsed release implant (ie as an additional film applied over the N polymer, see FIG. 1). This removes the necessity of using two implants (immediate release, and delayed pulsed release).

(ii) particles or pellets sprayed with the N/S film combination to achieve delayed pulsed release.

Figures 6, 6A:
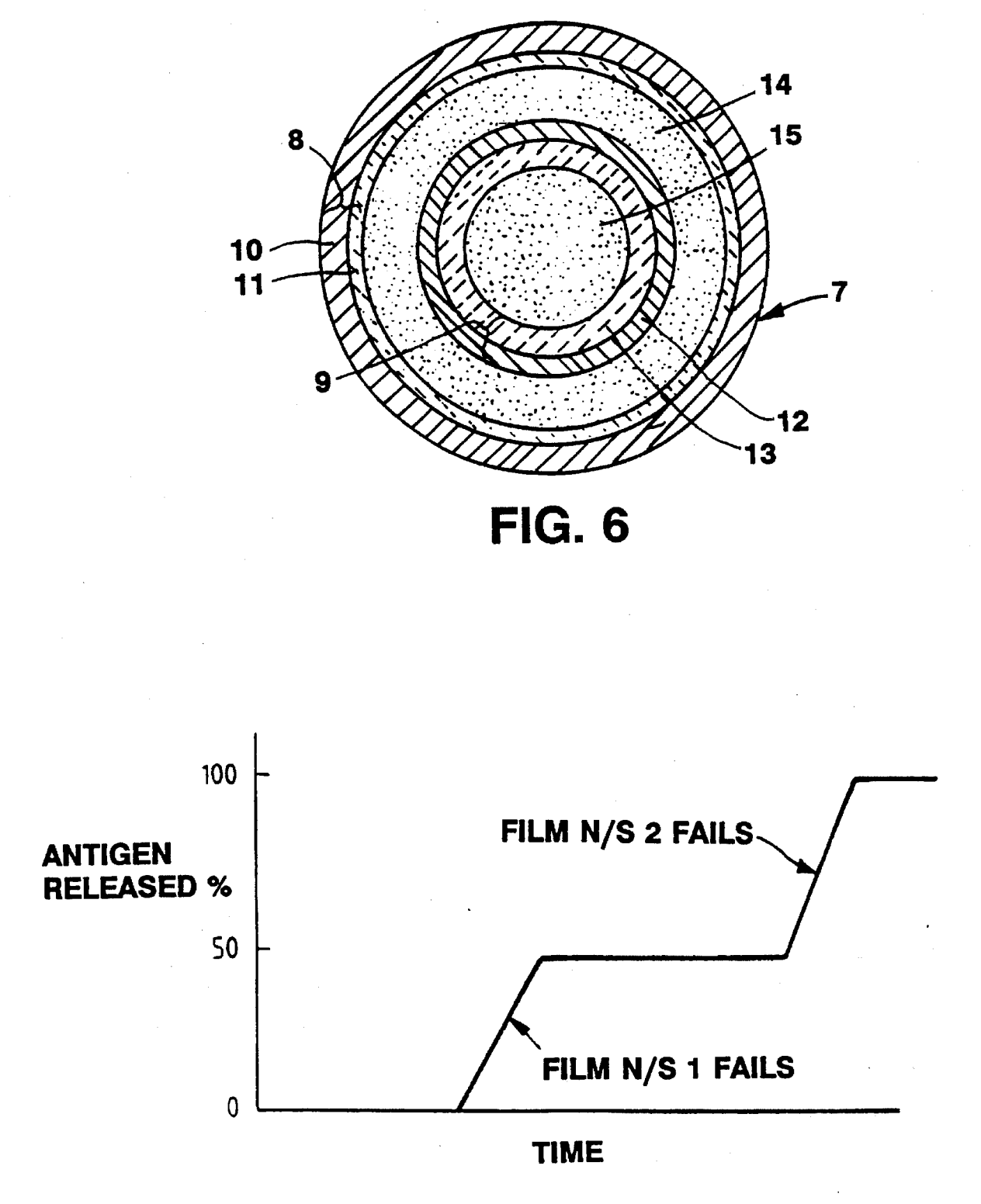

(iii) particles, pellets or implants sprayed with two N/S film combinations separating two antigen/adjuvant payloads, to give two delayed pulsed doses separated by a time interval. FIG. 6 shows such an implant 7, in which two N/S film combinations 8 and 9, each of which has an outer, insoluble film (10 and 12 respectively) and an inner, soluble film (11 and 13 respectively), separate two antigen/adjuvant payloads 14 and 15. The time course of antigen release from such an implant is illustrated in FIG. 6A.

(iv) delayed pulsed release implants as described in Example 2 (FIG. 1), but containing coated pellets/particles in the core to give a second delayed pulsed release of antigen.

(v) as described in (iv), but using bioerodible pellets (e.g. lactide/glycolide copolymers) in the core to achieve delayed pulsed release.

Those skilled in the art will appreciate that the invention described herein is susceptible to variations and modifications other than those specifically described. It is to be understood that the invention includes all such variations and modifications which fall within its spirit and scope.

The following terms used herein are registered trade marks:

Emcompress,

Explotab,

Eudragit,

Montanide, and

Lactel.

References cited herein are listed on the following pages.

[1] Penny R. "The Complete Guide to Immunisation, Part I: Understanding the Immune Process" Current therapeutics, August 1989 p65.

[2] Robinson J. R. and Lee V. H. (editors) "Controlled Drug Delivery, Fundamentals and Applications" (Drugs and the pharmaceutical sciences, vol 29) Edition 2, Marcel Dekker, 1987.

[3] Tyle P. (editor) "Drug Delivery Devices, Fundamentals and Applications" (Drugs and the pharmaceutical sciences, vol 32) Marcel Dekker, 1988.

[4] Carter D. H., Luttinger M. and Gardner D. L. "Controlled release parenteral systems for veterinary applications" Journal of Controlled Release 8 (1988) 15–22.

[5] Langer R. "Novel drug delivery systems" Chemistry in Britian, March (1990) 232–236.

[6] Chien Y. W. "Novel Drug Delivery Systems, Fundamentals, Developmental Concept, Biomedical Assessments" (Drugs and the pharmaceutical sciences, vol 14) Marcel Dekker, 1982.

[7] Marcotte N. and Gossen M. F. A. "Delayed release of water-soluble macromolecules from polylactide pellets" Journal of Controlled Release 9 (1989) 75–85.

[8] Oppenheim R. C., Tsui K. C., Lam L. F. and Thiel W. J. "Fluid uptake and drug release from a 30 mg coated implant" Proceed. Intern. Symp. Control. Rel. Bioact. Mater., 15 (1988) p52, Controlled Release Society Inc.

[9] Oppenheim R. C., Thiel W. J., Staples L. D., Williams A. H. and Clarke I. J. "Release of Peptides from Coated Implants" Proceed. Intern. Symp. Control. Rel. Bioact. Mater. 15 (1988) p54, Controlled Release Society Inc.

[10] Conte U., Colombo P., La Manna A. and Gazzaniga A. "A new pulsed release oral dosage form" Drug Development and Industrial Pharmacy 15 (1989) 2583–2596.

[11] Ueda S., Ibuki R., Hata T. and Ueda Y. "Design and development of time-controlled explosion system (TES) as a controlled drug release system" Proceed. Intern. Symp. Control. Rel. Bioact. Mater. 15 (1988) p450, Controlled Release Society Inc.

[12] Cohen S., Chow M. and Langer R. "Microencapsulated Liposomes—A Potential System for Vaccine Delivery" Proceed. Intern. Symp. Control. Rel. Bioact. Mater. 16 (1989) p71.

[13] "Handbook of Pharmaceutical Excipients" American Pharmaceutical Association and The Pharmaceutical Society of Great Britain (joint publication) 1988.

[14] McGinity J. W. (editor) "Aqueous Polymeric Coatings for Pharmaceutical Dosage Forms" (Drugs and the Pharmaceutical Sciences, Vol 36), Marcel Dekker, 1989, Chapters 4 and 5.

[15] Blood D. C. and Radostits O. M. "Veterinary Medicine, A textbook of Diseases of Cattle, Sheep, Pigs, Goats and Horses" 7th Edition, Bailliere Tindall, 1989.

[16] Baker R. "Controlled Release of Biologically Active Agents" John Wiley & Sons, 1987.

[17] Chasin M. and Langer R. (editors) "Biodegradable Polymers as Drug Delivery Systems" (Drugs and the Pharmaceutical Sciences, Vol 45) Marcel Dekker, 1990, Chapter 1.

[18] Christensen F. N. and Bertelsen P. "Discussion of A New Method For Stabilizing The Release From A Water-Based Release-Controlling Membrane", Proceed. Intern. Symp. Control. Rel. Bioact. Mater. 17 (1990) Controlled Release Society, Inc.

[19] Kost J. (editor) "Pulsed and Self Regulated Drug Delivery" CRC Press, 1990, Chapter 5.

We claim:

1. A pharmaceutical or veterinary implant, which when parenterally administered releases a pulse of at least one biologically active material at a controllable time interval after implantation, said implant comprising:

a) a core comprising the biologically active material and a tabletting excipient comprising at least one water soluble material and at least one water insoluble swellable material; and, b) at least one polymer film coating adapted to rupture at a predetermined time after implantation, said coating being permeable or semi-permeable to physiological fluid and essentially surrounding said core and preventing release of the core prior to rupture, wherein said excipient and said at least one polymer film coating are biocompatible.

2. An implant according to claim 1, in which the biologically active material is selected from the group consisting of antigens, antibodies, hormones, growth promotants, antibiotics, nutrients, minerals and vitamins.

3. An implant according to claim 1, in which the excipient comprises a combination of two or more water-soluble and water-insoluble materials.

4. An implant according to claim 3, in which the water-insoluble material is swellable.

5. An implant according to claim 1 wherein two different polymer film coatings are applied to a compressed core, and said polymer film coatings are:

i) a bilayer coating comprising an insoluble biocompatible film and an enteric (pH sensitive) polymer, or ii) a single film comprising a mixture of insoluble and biodegradable polymer.

6. An implant according to claim 1, in which the polymer film coating comprises a mixture of water insoluble and biodegradable polymers.

7. A pharmaceutical or veterinary implant which when parenterally administered releases a biologically active material in a delayed pulsed release manner, wherein the implant comprises the biologically active material and excipients as a compressed or moulded core encased within a polymeric coating which degrades sufficiently after a period of time to release the biologically active material, wherein all of the implant components are biocompatible.

8. A combined pharmaceutical or veterinary implant comprising an implant according to claim 1, further comprising the same or a different biologically active material formulated for release with substantially no delay when said implant is parenterally administered.

9. An implant according to claim 1, wherein the biologically active material is an antigen.

10. An implant according to claim 9, which additionally comprises an immunologically active adjuvant.

11. An implant according to claim 9 or claim 10 wherein the antigen is selected from the group consisting of caseous lymphadenitis toxoid, *Clostridium botulinum* toxoid, tetanus toxoid, and luteinizing hormone releasing hormone.

12. An implant according to claim 1, wherein the biologically active material is a hormone, a vitamin and a growth promotant.

13. A method of administration of a biologically active material to a mammal, comprising the step of parenterally implanting into said mammal an implant wherein the implant comprises:

a) a core comprising the biologically active material and a tabletting excipient comprising at least one water soluble material and at least one water insoluble swellable material; and, b) at least one polymer film coating adapted to rupture at a predetermined time after implantation, said coating being permeable or semi-permeable to physiological fluid and essentially surrounding said core and preventing release of the core prior to rupture, wherein said excipient and said at least one polymer film coating are biocompatible.

14. An implant according to claim 1 wherein the polymer film coating is adapted to rupture at 9–60 days after implantation.

15. An implant according to claim 1 or claim 7, wherein the pulse of biologically active material is a first pulse, and the first pulse is followed by a second pulse of the same or a different biologically active material at a controllable time interval after the first pulse.

* * * * *